US005981823A

United States Patent [19]

Turngren

[11] Patent Number: 5,981,823

[45] Date of Patent: Nov. 9, 1999

[54] STERILE ADHESIVE BANDAGE AND ASSOCIATED METHODS

[75] Inventor: Christina Margaret Turngren, St. Paul, Minn.

[73] Assignee: RUA, Inc., Edina, Minn.

[21] Appl. No.: 08/966,601

[22] Filed: Nov. 10, 1997

Related U.S. Application Data

[63] Continuation of application No. 08/557,950, Nov. 14, 1995, Pat. No. 5,685,833.

[51] Int. Cl.[6] .............................. A61F 13/00; A61F 15/00

[52] U.S. Cl. ................................ 602/58; 602/41; 602/57; 602/900; 206/440; 206/441

[58] Field of Search .................................... 206/440, 441; 602/41–57; 128/888, 889

[56] References Cited

U.S. PATENT DOCUMENTS

| | | | |
|---|---|---|---|
| 1,827,354 | 10/1931 | Cooper . | |
| 2,862,846 | 12/1958 | Blackford et al. | 154/118 |
| 3,520,403 | 7/1970 | Moshel | 206/63.2 |
| 3,531,847 | 10/1970 | Wallerstein | 29/411 |
| 3,835,992 | 9/1974 | Adams, IV | 206/390 |
| 4,161,176 | 7/1979 | Harris, III et al. . | |
| 4,600,001 | 7/1986 | Gilman . | |
| 4,733,797 | 3/1988 | Haber | 221/8 |
| 4,807,753 | 2/1989 | Goldstein | 206/390 |
| 4,830,183 | 5/1989 | Metters | 206/441 |
| 4,867,821 | 9/1989 | Morgan | 156/152 |
| 4,884,563 | 12/1989 | Sessions . | |
| 4,954,210 | 9/1990 | Desmond | 156/584 |
| 4,993,596 | 2/1991 | Taulbee et al. | 221/25 |
| 5,018,516 | 5/1991 | Gilman . | |
| 5,065,894 | 11/1991 | Garland | 221/25 |
| 5,133,477 | 7/1992 | Etheredge, III et al. | 221/25 |
| 5,133,821 | 7/1992 | Jensen | 156/245 |
| 5,160,315 | 11/1992 | Heinecke et al. | 602/57 |
| 5,197,493 | 3/1993 | Grier-Idris | 128/853 |
| 5,271,522 | 12/1993 | Ko et al. | 221/58 |
| 5,336,162 | 8/1994 | Ota et al. | 602/41 |
| 5,501,661 | 3/1996 | Cartmell et al. | 602/58 |
| 5,511,689 | 4/1996 | Frank | 221/73 |
| 5,520,629 | 5/1996 | Heinecke et al. | 602/57 |
| 5,531,855 | 7/1996 | Heinecke et al. | 156/252 |
| 5,709,651 | 1/1998 | Ward | 602/57 |
| 5,722,943 | 3/1998 | Sessions | 602/57 |

*Primary Examiner*—Richard J. Apley
*Assistant Examiner*—Kim M. Lee
*Attorney, Agent, or Firm*—Nikolai, Mersereau & Dietz, P.A.

[57] ABSTRACT

A bandage encapsulated in a protective sterile covering is disclosed, whereby the bandage may be removed from its sterile covering and applied with one hand without contaminating any portion of the bandage. The apparatus and method to manufacture the unique bandage is also disclosed.

16 Claims, 5 Drawing Sheets

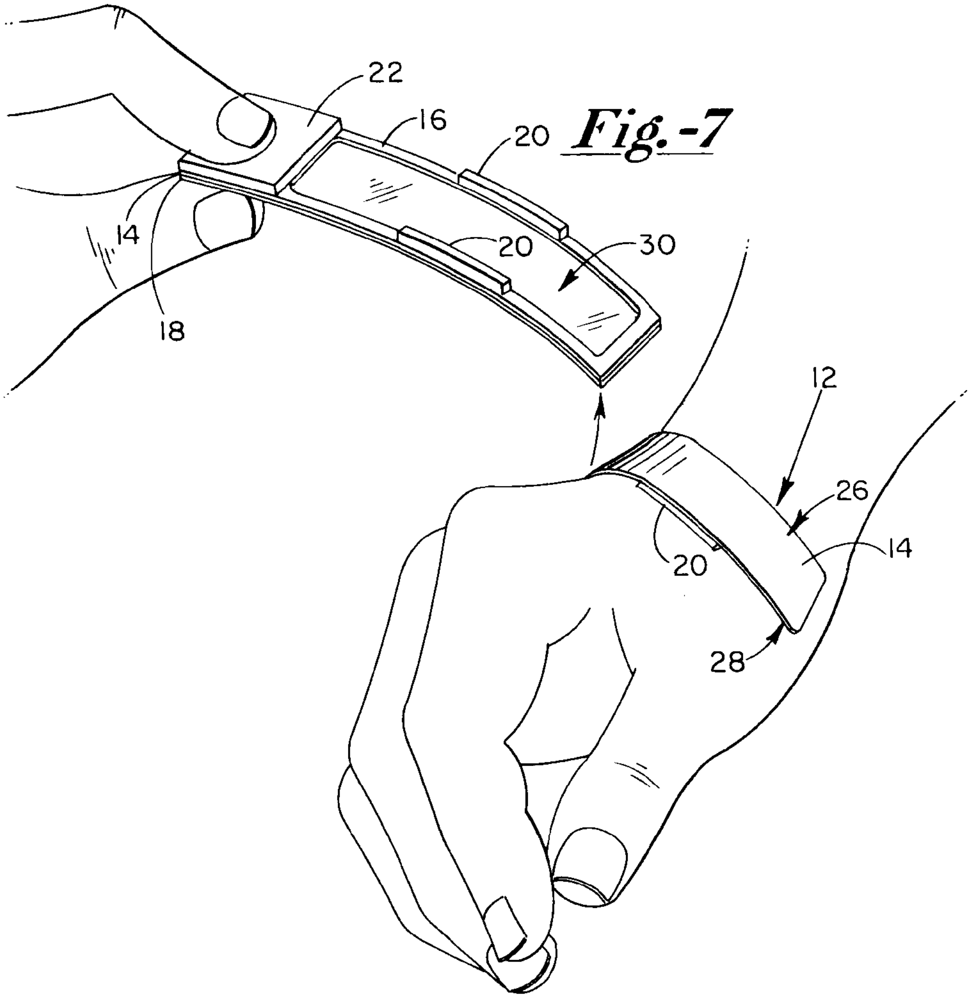
Fig.-7
Fig.-8
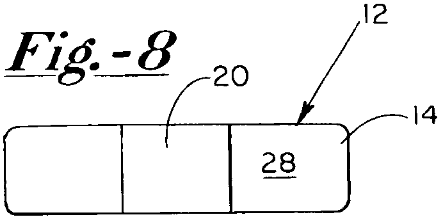

STERILE ADHESIVE BANDAGE AND ASSOCIATED METHODS

This is a Continuation application of application Ser. No. 08/557,950, filed on Nov. 14, 1995 now U.S. Pat. No. 5,685,833.

BACKGROUND OF THE INVENTION

I. Field of the Invention

This invention relates generally to an apparatus for enclosing a sterile device. More particularly, this invention relates to a sterile adhesive bandage, encapsulated in a protective covering. The protective covering may be removed and the sterile bandage may be applied by a user with just one hand without contaminating any portion of the sterile bandage. This invention also relates to the method and apparatus for producing the sterile adhesive bandage contained in the protective covering, wherein the bandage may be removed from the protective covering and applied by the user with one hand.

II. Discussion of the Related Art

Over the years, continued refinements have been made to dispensing bandages and other sterile devices. A plurality of sterile devices are commonly contained in an interconnected series of sterile packages. Removing each sterile device from the package requires contact by the user. Protective gloves may be worn during the removal and handling of the sterile device thereby avoiding contamination, however, the use of sterile gloves is often times neither economical nor efficient.

Various delivery systems have been described that assist the user in removing an individual sterile device from the package with only one hand. The following patents describe a delivery system that dispense the sterile device, requiring only one hand by the user: Haber, U.S. Pat. No. 4,733,797 (the '797 patent); Goldstein, U.S. Pat. No. 4,807,753 (the '753 patent); Moshel, U.S. Pat. No. 3,520,403 (the '403 patent); and Cooper U.S. Pat. No. 1,827,354 (the '354 patent). Although these disclosed delivery systems dispense the sterile device, requiring only one hand, the user must use two hands in the later application of the sterile device. Hence, there is a need for a packaged sterile device that may be dispensed and applied with only one hand.

A commonly packaged sterile device is an adhesive bandage. The conventional bandage includes a gauze pad attached to an adhesive coated bandage strip. When applying the bandage to the desired surface, the user removes the adhesive bandage from the sterile package, contacting either the sterile gauze or a portion of the adhesive strip. This contact either contaminates the gauze pad or reduces the tactile adhesion of the adhesive strip.

Taulbee, deceased et al., in U.S. Pat. No. 4,993,586 (the '586 patent), and Adams IV, U.S. Pat. No. 3,835,992 (the '992 patent) both disclose an adhesive bandage dispensing package. Taulbee discloses an adhesive bandage sandwiched between an upper and lower protective strip. The adhesive side of the bandage is mounted facing downward on the lower protective strip. One end of the adhesive strip preferably attaches to a mounting pad. The mounting pad facilitates removal of the bandage from the lower protective strip, however, two hands are required to remove the mounting pad from the adhesive strip, and a portion of the sterile bandage must be contacted by the user. Therefore, a need exists for a sterile device, such as a bandage that may be dispensed and applied with one hand without contaminating any portion of the sterile device.

Adams, IV, discloses a bandage dispensing package similar to Taulbee, which dispenses a bandage from a continuous roll. A similar mounting pad separates one end of the adhesive strip from the lower protective strip. In use, the user must use two hands to separate the mounting pad from the adhesive strip. Hence, there is a need for a bandage that may be dispensed and applied with only one hand. The present invention overcomes these and other disadvantages.

SUMMARY OF THE INVENTION

The purpose of the present invention is to provide a bandage that may be applied without contaminating any portion of the bandage. In the preferred embodiment, the bandage can further be applied with a single hand without contaminating any portion of the bandage. The bandage is enclosed in a sealed sterile package, whereby the bandage may be removed from the package and applied to a desired surface with only one hand. The sterile package, including the bandage, comprises a flexible strip, a carrier member, a wound pad, a pull tab, and a release backing.

The flexible strip has a coating of adhesive deposited on at least the lower planar surface of the strip. A wound pad is attached to the lower planar surface of the strip and centered such that a portion of the adhesive strip extends from each end of the wound pad. The wound pad and strip are die cut in a predetermined shape, thereby separating the wound pad and strip into an outer surrounding frame and inner bandage. The pull tab is further attached to a lower planar surface of the outer surrounding frame, proximate an end of the flexible strip.

The flexible strip, wound pad, and pull tab are sandwiched between a carrier member and a release backing. The carrier member has a light tack adhesive, thereby attaching to an upper surface of both the bandage and outer surrounding frame of the adhesive strip. The release backing adheres to the lower surface of the flexible, adhesive strip.

In the preferred embodiment, a plurality of bandages and outer surrounding frames, each having a carrier member attached thereto, are attached in series to a continuous roll of release backing. The bandages may be individually dispensed from the roll. As the bandage is dispensed, the bandage, outer frame and carrier member separate from the release backing.

The user centers the wound pad over the desired location and presses the tab and an adjacent portion of the adhesive strip against the desired surface. The remaining portion of the adhesive strip is pressed against the desired surface. By holding onto the pull tab, the user avoids any contaminating contact with the bandage, including cross-contamination of the upper surface of the bandage. The pull tab is then pulled away from the surface, separating the pull tab and outer frame of the adhesive strip from the bandage. The outer frame of the bandage and carrier member separates from the bandage leaving the bandage affixed to the desired surface. In this manner only one hand is required to dispense the bandage and apply the bandage to the desired surface.

During the manufacture of the continuous roll of bandages a sheet of adhesive may be used to form in rows and columns a plurality of interconnected bandages. The columns of bandages formed on the sheet may be separated, to thereby form a plurality of continuous rolls of bandages.

In an alternate preferred embodiment, each bandage and outer frame are attached to an independent release backing. A plurality of these bandages may be indexed and dispensed independently. The pull tab is not attached to the release backing, which aids the user in easily removing the release backing from the bandage and outer frame.

In another alternate preferred embodiment the flexible strip is constructed of a litmus paper, eliminating the need for a wound pad. The litmus paper may be removed from its package similar to the removal of the bandage, thereby avoiding any contaminating contact to the paper.

It is accordingly a principal object of the present invention to provide a sterile adhesive bandage that may be removed from its package and applied with a single hand without any contaminating contact to the bandage's adhesive strip or wound pad.

Another object of the present invention is to provide a sterile litmus paper that may be removed from its package without any contaminating contact to the litmus strip.

Still a further object of the present invention is to provide a method of manufacturing a sterile bandage that may be dispensed and applied by the user without contaminating the bandage.

Still another object of the present invention is to provide a method for manufacturing a continuous roll of interconnected bandages that may be separated individually, dispensed, and applied by the user using only one hand.

Still a further object of the present invention is to provide a method of simultaneously manufacturing from a web sheet of adhesive material, a plurality of continuous rolls of bandages.

These and other objects, as well as these and other features and advantages of the present invention will become readily apparent to those skilled in the art from a review of the following detailed description of the preferred embodiment in conjunction with the accompanying claims and drawings in which like numerals in the several views refer to corresponding parts.

DESCRIPTION OF THE DRAWINGS

FIG. 7 is a perspective view of an individual bandage applied to a user's wrist;

FIG. 8 is a bottom plan view of an inner bandage removed from the outer surrounding frame and carrier member;

DETAILED DESCRIPTION OF THE PREFERRED EMBODIMENT

Figure 1:
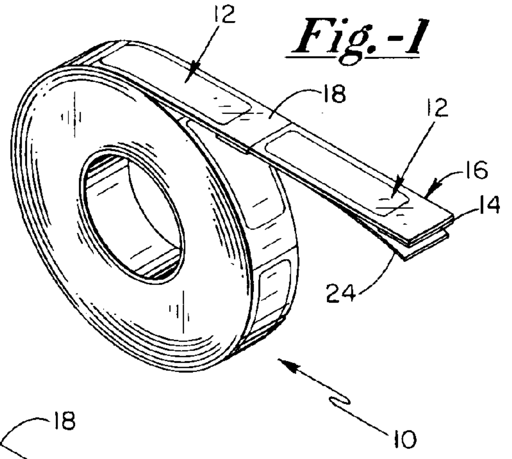
FIG. 1 is a perspective view of a plurality of interconnected bandages, forming a continuous roll of bandages.
Figure 2:
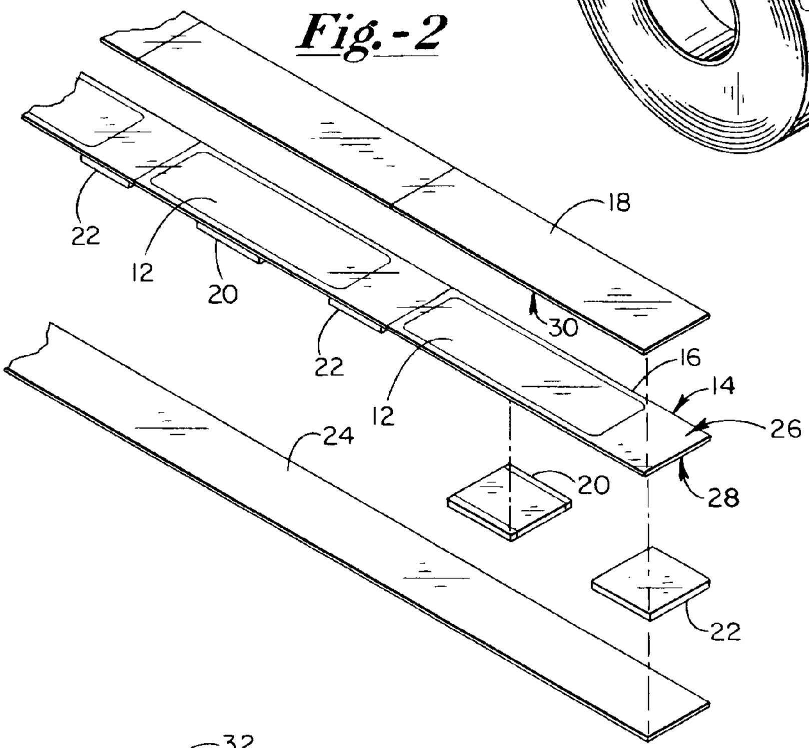
FIG. 2 is a partial exploded perspective view of interconnected bandages.

Referring first to FIGS. 1 and 2, there is shown generally a continuous roll 10 of bandages 12. Each bandage 12 consists generally of a flexible adhesive strip 14, an outer surrounding frame 16, a carrier member 18, a wound pad 20, a pull tab 22, and a release backing 24.

The wound pad 20 and pull tab 22 are attached to the lower planar surface 28 of the adhesive strip 14 (see FIGS. 2 and 8). The bandage 12 is die cut from the adhesive strip 14 and separated from the outer surrounding frame 16. A carrier member 18 is attached to the upper planar surface 26 of the bandage 12 and outer surrounding frame 16. For illustrative purposes, the die cut defining the shape of the bandage 12 is depicted as visible through the carrier member 18. Those skilled in the art will recognize that the carrier member may be manufactured from an opaque or transparent material. The lower planar surface 28 of the bandage 12 and outer surrounding frame 16 are attached a continuous roll of release backing 24, thereby forming a continuous roll 10 of interconnected bandages 12.

The flexible strip 14 has an adhesive, suited to medical applications, bonded to the lower planar surface 28 of the strip. Without limitation, the flexible strip 14 may be of a transparent or opaque: vinyl, woven fabric, non-woven fabric, or polyester material. An adhesive may be formed on the upper surface 26 of the flexible strip 14 or the lower surface 30 of the carrier member 18. In the preferred embodiment, an adhesive is bonded to the lower surface 30 of the carrier member 18. The adhesive is formulated so that when the bandage 12 is removed from the carrier member 18, the adhesive remains on the carrier member 18. Without limitation, this adhesive is a nontransferable light tack adhesive commonly known in the industry as high tack/low tack adhesive, and is available from Minnesota Mining and Manufacturing, Inc., St. Paul, Minn. The release backing 24 is preferably manufactured from a polymer, easily removable from the flexible strip's adhesive.

The pull tab 22 does not adhere to the release backing 24, allowing the user to easily remove the release backing from an individual bandage 12. When the bandage 12 and outer surrounding frame 16 are sandwiched between the carrier member 18 and the release backing 24, an air tight seal is formed, whereby the wound pad 20 and bandage 12 remain sterile.

Figure 3:
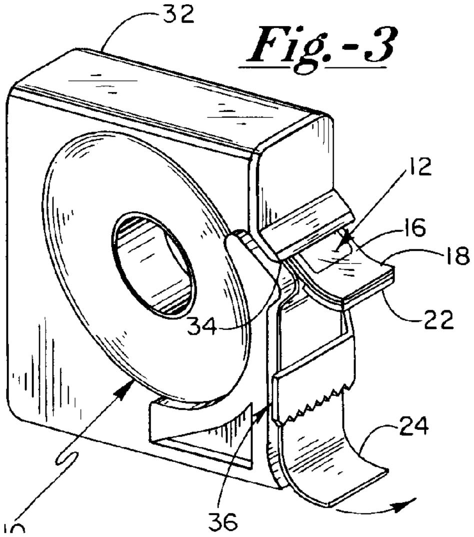
FIG. 3 is a perspective view of a continuous roll of bandages of the type shown in FIG. 1 being dispensed.

Referring next to FIG. 3, a continuous roll of bandages 10 is positioned within a dispenser 32, whereby the bandage 12 may be dispensed with only one hand. The bandage 12 is shown partially dispensed. As the user pulls on the pull tab 22, the bandage 12, outer surrounding frame 16, and carrier member 18, together, exit an opening 34 in the dispenser while the release backing 24 separates from the flexible adhesive strip 14 and is guided away through a guide channel 36. Each bandage 12, outer surrounding frame 16 and carrier member 18 are separated from the continuous roll 10 in a similar fashion.

Figure 4:
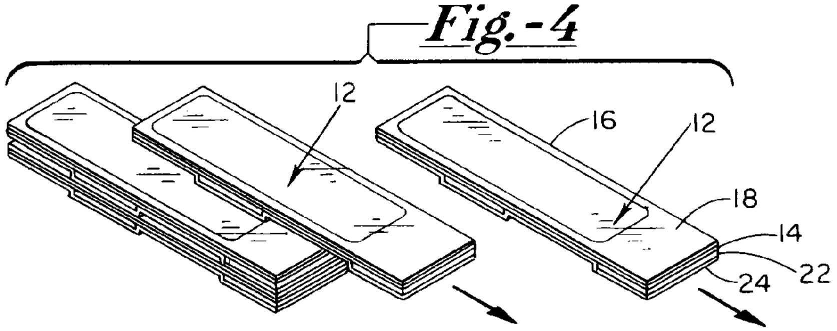
FIG. 4 is a perspective view of a plurality of individual indexed bandages.

An alternate preferred embodiment is shown in FIG. 4. Each bandage 12 and outer frame 16 are attached to an independent strip of release backing 24. A plurality of bandages 12 are shown indexed and dispensed independently, whereby the arrows aligned with the longitudinal axis of the bandage 12 indicate the dispensing motion and direction. When the user dispenses an individually indexed bandage 12, the pull tab 22 assists the user in easily removing the release backing 24 from the bandage 12 and outer frame 16.

Figure 5:
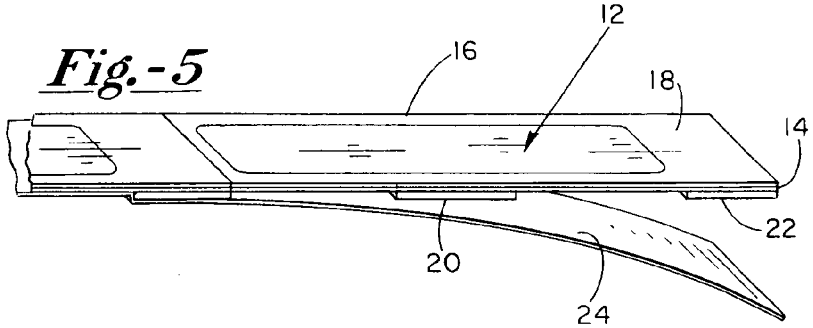
FIG. 5 is an enlarged partial perspective view of interconnected bandages having the release backing partially removed.
Figure 6:
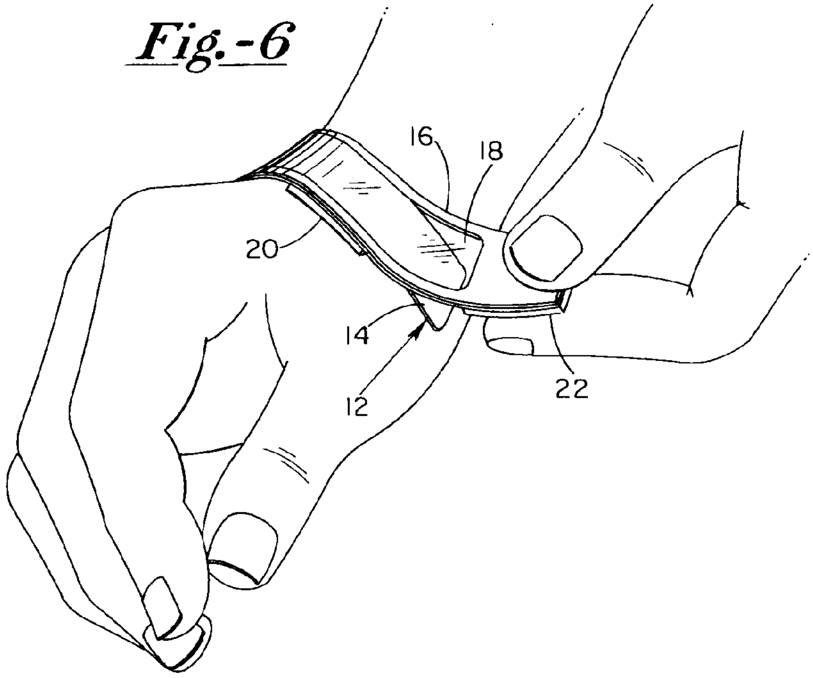
FIG. 6 is a perspective view of an individual bandage being applied to a patient's wrist.

FIGS. 5–7 further illustrate how the bandage 12 is separated from the release backing 24, carrier member 18 and outer frame 16. The release backing 24 is first removed from the lower planar surface 28 of the bandage 12 and outer surrounding frame 16 (see FIG. 5). The user then aligns the wound pad 20 over the desired surface and presses the adhesive strip 14 against the desired surface. The user then pulls the pull tab 22 away from the desired surface, towards the other end of the adhesive strip 14.

The bandage 12 separates from the carrier member 18, while adhering to the desired surface. The outer surrounding frame 16 remains attached to the carrier member 18, when the pull tab 22 is used to peel the outer frame 16 and carrier member 18 from the desired surface. In this manner only one hand is required to dispense and apply the bandage 12 to a desired surface.

Figure 9:
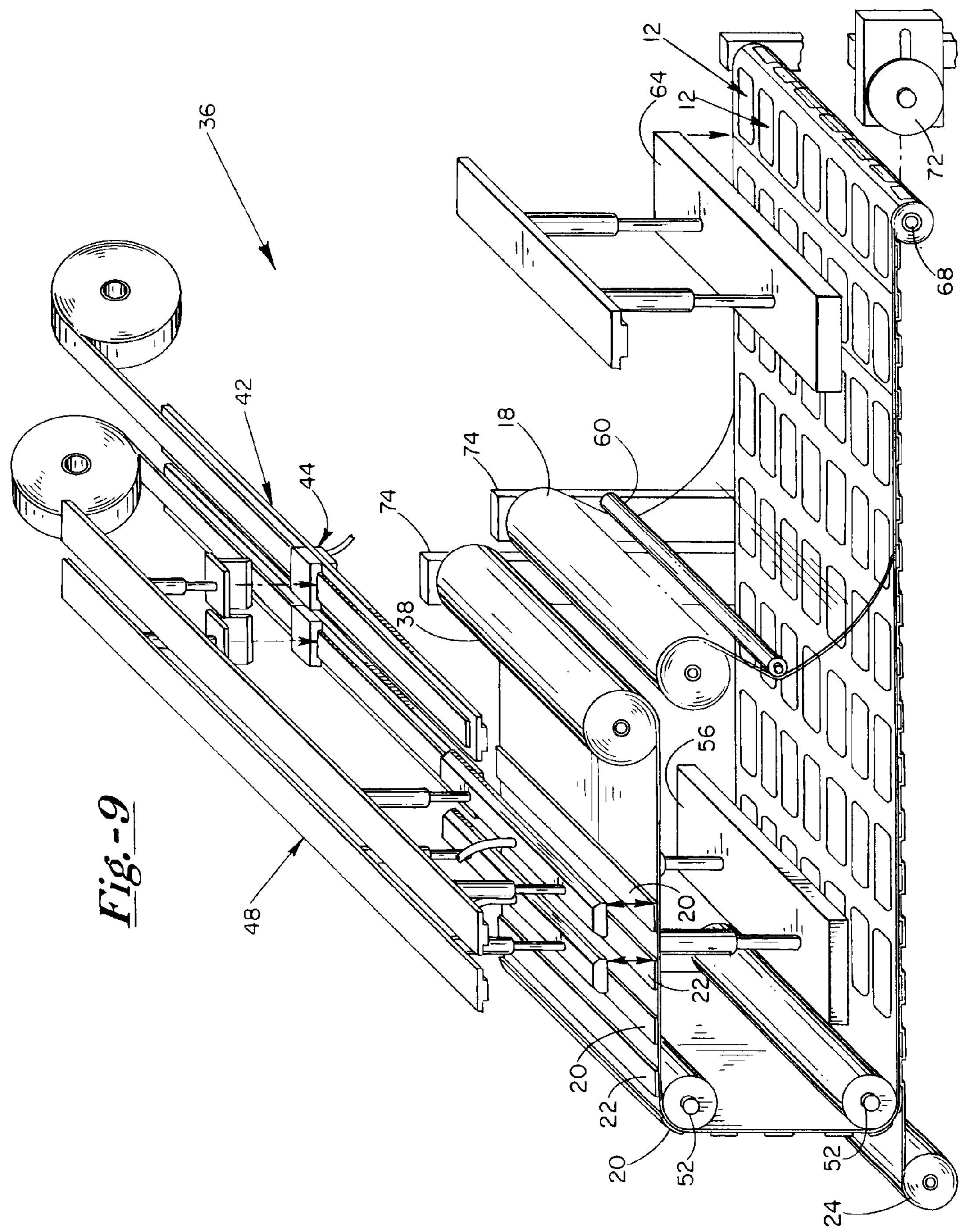
FIG. 9 is a perspective view, partially in block, of the apparatus for manufacturing the bandage and its package.
Figure 10:
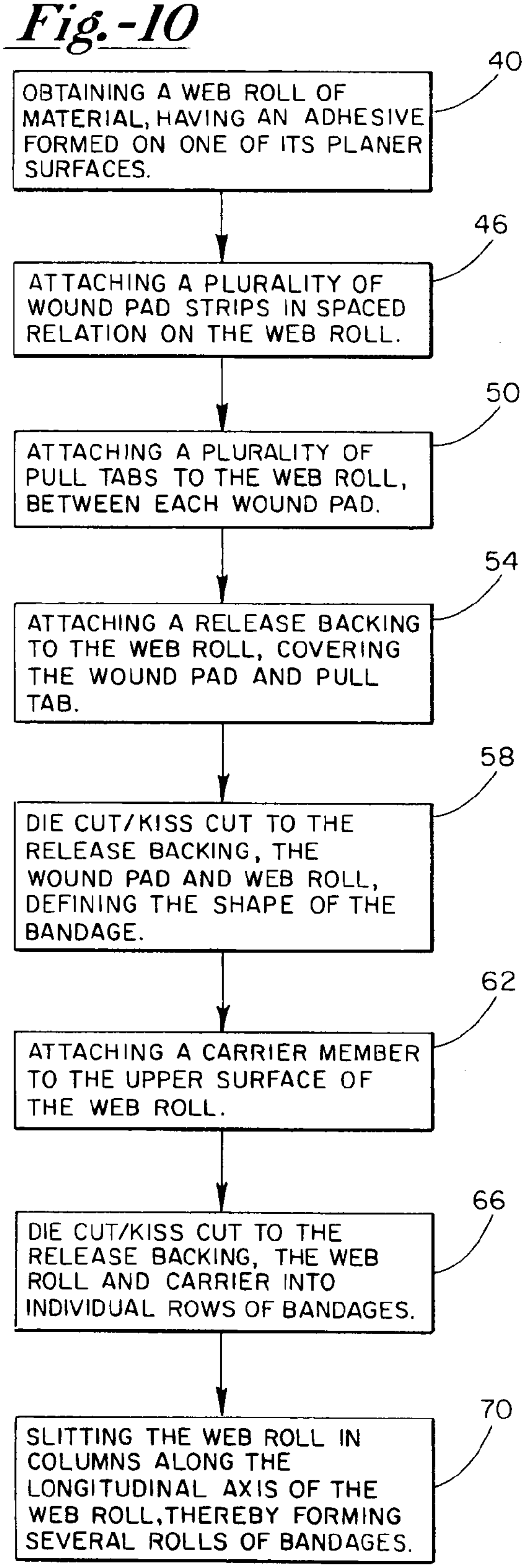
FIG. 10 is a flow diagram of the steps necessary to manufacture a plurality of continuous rolls of bandages roll of the type shown in FIG. 1.

Referring next to FIGS. 9 and 10, an apparatus 36 for manufacturing a plurality of continuous rolls of bandages 10 is generally shown and described. The apparatus 36 includes several stations that perform various functions on an adhesive strip 14 or web roll 38 being continuously fed therethrough, thereby forming continuous rolls of bandages 10.

After obtaining a sheet or web roll 38 of material having adhesive deposited on at least one planar surface (see block 40), the continuous web roll 38 is fed past a first station 42, wherein a vacuum placing system 44, of known construction, systematically places strips of wound pad 20 in spaced relation on the adhesive surface of the web roll 38 (see block 46). In an alternate preferred embodiment, individual wound pads 20 are systematically placed on the adhesive surface of the web roll 38 and arranged in island placement. When the wound pad 20 is arranged on the web by island placement, a portion of the adhesive strip extends from the wound pad 20 from all sides of the wound pad.

The web roll 38 continues forward to a second station 48, where strips of pull tab 22 are systematically positioned and attached to the web roll 38. The pull tab 22 is positioned on the web roll 38 a predetermined distance from each wound pad 20 (see block 50). Of course, an additional pull tab 22 may be attached and positioned a predetermined distance from each wound pad 20, such that a pull tab 22 will be attached at each end of the adhesive strip 14.

Those skilled in the art will recognize that the vacuum placing system 44 may either simultaneously or individually place the wound pad 20 and pull tab 22 on the adhesive surface of the web roll 38. The vacuum placing system as shown, has two independent vacuum plates, however, those skilled in the art will recognize that one vacuum plate may be used to place the wound pad 20 and pull tab 22 on the adhesive surface of the web roll 28 in spaced relation, either simultaneously or independently.

Guide rollers 52 direct the web roll 38 over a sheet roll of release backing 24, whereby the release backing 24 is pressed against the lower adhesive surface 14 of the adhesive strip 14 or web roll 38. The release backing 24 is thereby attached to the web roll 38, sealably covering the wound pad 20 and pull tab 22 (see block). A first die 56 of known construction having a predetermined shape die cut/ kiss cuts the wound pad 20 and web roll 22 to the release backing into a plurality of bandages having predetermined shapes (see block 58).

The carrier member 18 is guided into contact with the web roll 38 and release backing 24 by guide roller 60 (see block 62). The carrier member 18 adheres to the upper surface 26 of the web roll 38, thereby sealing the web roll 38 between the carrier member 18 and the release backing 24. A second die-cutter 64 of known construction die cut/kiss cuts to the release backing the web roll and carrier member along their widths, thereby defining rows of bandage strips (see block 66). Finally, as the compressed web roll 38, carrier member 18 and release backing 24 are rolled onto a spool 68, a slitter 72 slits the compressed web roll 38, carrier member 18 and release backing 24 along their longitudinal axis, thereby forming several continuous rolls of interconnected bandages 10 (see block 70). Those skilled in the art will recognize that the various stations may be connected to a central frame 74 or connected to several integral frames. Once a desired length of the continuous roll is rolled onto the spool 68 which rotates on a spindle 74, a slicer or cutter separates the roll, and the several continuous rolls are removed from the spindle.

This invention has been described herein in considerable detail in order to comply with the patent statutes and to provide those skilled in the art with the information needed to apply the novel principles and to construct and use such specialized components as are required. However, it is to be understood that the invention can be carried out by specifically different devices, and that various modifications, both as to the equipment details and operating procedures, can be accomplished without departing from the scope of the invention itself.

What is claimed is:

1. A device including a strip that may be removed from its sealed enclosure without contaminating any portion of the strip, comprising:

(a) a planar strip being die cut to define a shape of the strip;

(b) a removable carrier member attached to an upper planar surface of said strip, wherein said carrier member engages the upper planar surface of said strip;

(c) a pull tab attached to a lower planar surface of said carrier member; and (d) a removable release backing attached to a lower planar surface of said strip, wherein said release backing engages the lower planar surface of said strip, and further wherein an outer perimeter edge of said carrier member and said release backing at least one of aligns and extends past an outer perimeter of said strip such that said strip is sealed between said release backing and said carrier member.

2. The device as recited in claim 1, wherein the strip has an adhesive coating deposited on a lower planar surface of said strip.

3. The device as recited in claim 2, further including a wound pad attached to the lower planar surface of said strip, wherein said wound pad is centered on the lower planar surface of said strip.

4. The device as recited in claim 1, wherein a plurality of strips having carrier members attached are aligned and attached in series to a continuous roll of release backing.

5. The device as recited in claim 1, wherein a plurality of strips having carrier members attached thereto are aligned and attached in rows and columns to a continuous sheet roll of release backing.

6. The device as recited in claim 1, wherein the carrier member has a light tack adhesive coating deposited on a lower strip engaging surface of said carrier member and the strip has an adhesive coating deposited on the lower planar surface of said strip.

7. The device as recited in claim 6, further including a wound pad attached to the lower planar surface of said strip, wherein said wound pad is centered on the lower planar surface of said strip.

8. The device as recited in claim 1, wherein said strip is manufactured from a material selected from the group consisting of vinyl, woven fabric, non-woven fabric, and polyester.

9. A delivery device including a sterile strip that may be removed from its sealed enclosure without contaminating any portion of the strip, said device comprising:

(a) a strip being die cut to define a shape of the strip;

(b) a wound pad attached to a lower planar surface of said strip;

(c) a removable carrier member attached to an upper planar surface of said strip, wherein said carrier member engages the upper planar surface of said strip;

(d) a pull tab associated with a lower planar surface of said carrier member; and (e) a removable release backing engaged with a lower planar surface of said strip, wherein an outer perimeter of said release backing engages the lower planar surface of said strip, and further wherein an outer perimeter edge of said carrier member and said release backing at least one of aligns and extends past an outer perimeter of said strip such that said strip is isolated in a sterile, sealed, environment between said release backing and said carrier member.

10. The device as recited in claim 9, wherein the carrier member has a light tack adhesive coating deposited on a lower strip engaging surface of said carrier member.

11. The device as recited in claim 9, wherein the strip has an adhesive coating deposited on the lower planar surface of said strip.

12. The device as recited in claim 9, wherein a plurality of strips having carrier members attached are aligned and attached in series to a continuous roll of release backing.

13. The device as recited in claim 9, wherein a plurality of strips having carrier members attached thereto are aligned and attached in rows and columns to a continuous sheet roll of release backing.

14. The device as recited in claim 9, wherein the carrier member has a light tack adhesive coating deposited on a lower strip engaging surface of said carrier member and the strip has an adhesive coating deposited on the lower planar surface of said strip.

15. The device as recited in claim 14, further including a wound pad attached to the lower planar surface of said strip, wherein said wound pad is centered on the lower planar surface of said strip.

16. The device as recited in claim 9, wherein said strip is manufactured from a material selected from the group consisting of vinyl, woven fabric, non-woven fabric, and polyester.

* * * * *